United States Patent [19]

Southern

[11] Patent Number: 5,667,667

[45] Date of Patent: Sep. 16, 1997

[54] ELECTROCHEMICAL TREATMENT OF SURFACES

[75] Inventor: Edwin Southern, Oxford, United Kingdom

[73] Assignee: Isis Innovation Limited, Oxford, England

[21] Appl. No.: 660,946

[22] Filed: Jul. 18, 1996

Related U.S. Application Data

[63] Continuation of Ser. No. 325,337, filed as PCT/GB93/00857, Apr. 23, 1993 published as WO93/22480, Nov. 11, 1993, abandoned.

[30] Foreign Application Priority Data

Apr. 24, 1992 [GB] United Kingdom ............... 9208921

[51] Int. Cl.[6] .................................................. C25F 1/00
[52] U.S. Cl. ..................... 205/687; 205/688; 205/698; 205/699; 205/766; 204/267; 204/412
[58] Field of Search ................................ 205/687, 688, 205/698, 699, 766; 204/267, 412

[56] References Cited

U.S. PATENT DOCUMENTS

| | | | |
|---|---|---|---|
| 4,466,864 | 8/1984 | Bacon et al. | 204/15 |
| 5,296,125 | 3/1994 | Glass et al. | 204/153.21 |
| 5,312,762 | 5/1994 | Guiseppi-Elie | 436/149 |
| 5,387,329 | 2/1995 | Foos et al. | 204/415 |

OTHER PUBLICATIONS

A.J. Bard et al., *Acc. Chem. Res.*, 23, 357–363 (1990) (no month).

Patent Abstracts of Japan, unexamined applications, C field, vol. 9, No. 12, The Patent Office Japanese Government, p. 60C261, No. 59-162290 (Jan. 18, 1985).

*Primary Examiner*—Arun S. Phasge
*Attorney, Agent, or Firm*—Wenderoth, Lind & Ponack

[57] ABSTRACT

A method of electrochemically patterning a surface comprises providing an electrolyte overlying the surface and an array of electrodes adjacent the surface and in contact with the electrolyte, and altering the potential of one or more electrodes of the array so as to deposit or remove or chemically modify a substance on the surface adjacent the electrode. Several such treatments can be performed in sequence, using different electrodes of the array. The method is particularly suitable for step-wise chemical synthesis e.g. of oligonucleotides or other oligomers tethered to the surface. Electrode arrays for use in the method are also claimed.

13 Claims, 2 Drawing Sheets

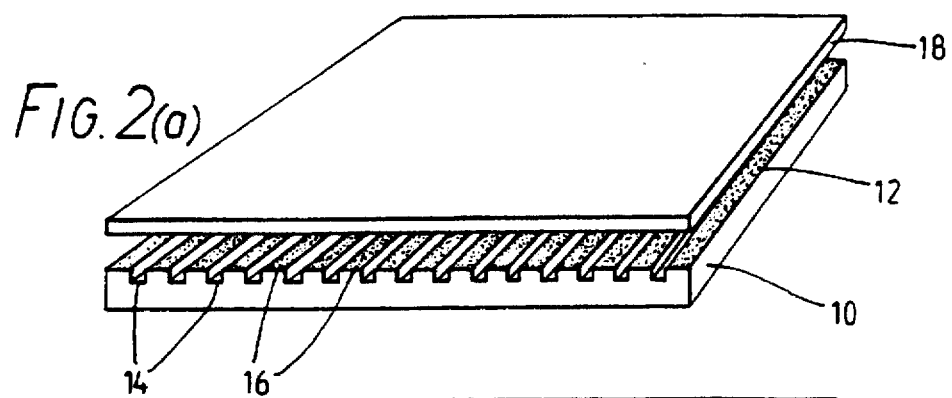
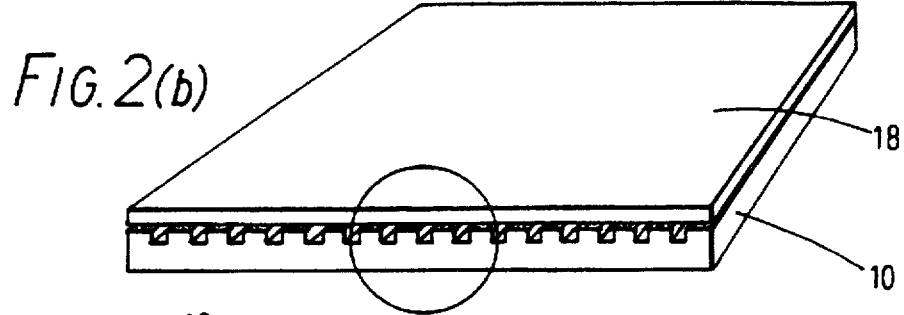
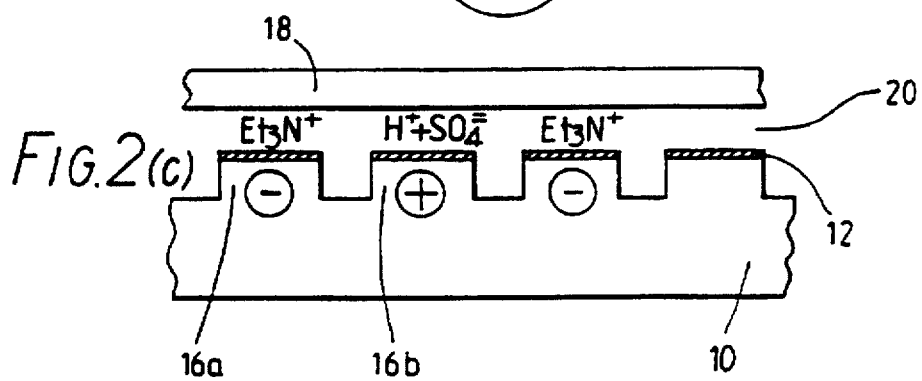
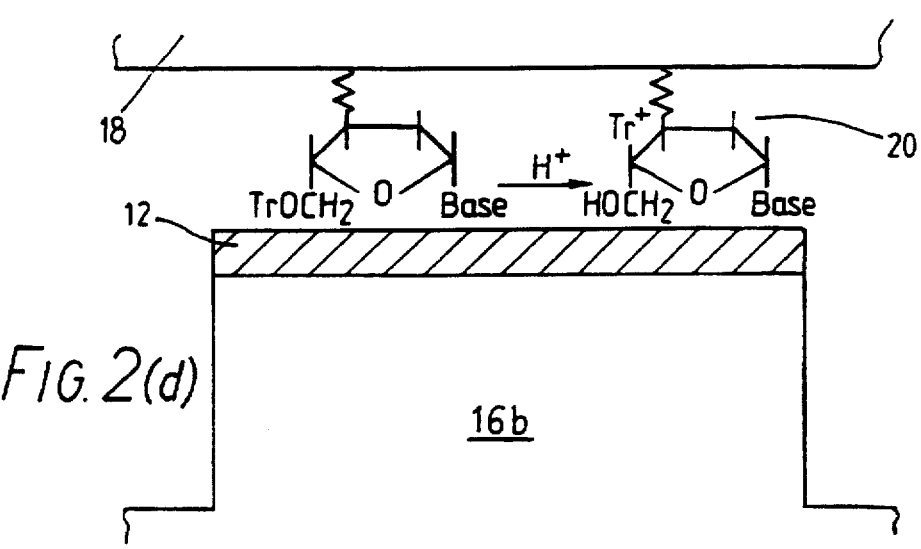

ELECTROCHEMICAL TREATMENT OF SURFACES

This application is a continuation of now abandoned application Ser. No. 08/325,337, filed Dec. 9, 1994 now abandoned, which is a 371 of PCT/GB93/00857, filed Apr. 23, 1993, published as WO93/22480, Nov. 11, 1993.

INTRODUCTION AND SUMMARY OF INVENTION

The ability to make devices with patterns of specific materials printed on the surface has transformed the manufacture of electronic and electrical components, and the discovery of new materials such as semiconductors has made possible devices for a wide range of applications. The properties of a device depend on the nature and the pattern of the materials on the surface and much research goes into devising new materials and new methods of fabrication, in order to improve production of existing devices and to develop devices with novel applications.

In one aspect, the invention provides a method of treating a region of a surface, which method comprises providing an electrolyte overlying the surface, an electrode adjacent the region of the surface to be treated and in contact with the electrolyte and a counter-electrode, and altering the potential of the electrode so as to deposit or remove or chemically modify a substance on the surface at the region adjacent the electrode, wherein the surface to be modified does not form either the electrode or the counter-electrode.

In another aspect the invention provides an array of electrodes, suitable for use in the stated method, comprising a block of insulating material having a surface, and deposits of electrically conducting material spaced apart in an array on the surface, each deposit being provided with electrical connecting means for altering its potential. Preferably the deposits of electrically conducting material are in the form of parallel-lines spaced apart by no more than 0.5 mm.

Preferably an array of electrodes is used to treat several regions of the surface simultaneously, and one or more of the electrodes of the array may be used as counter-electrodes. For the purpose of performing several electrochemical treatments in sequence, the electrodes of the array are preferably connected up so that each treatment is performed by altering the potential of a chosen set of one or more of the electrodes of the array.

Altering the potential of an electrode generally results in the generation of a reagent at the surface of the electrode. This reagent may itself be deposited on the surface. Or it may react with some other species, in the electrolyte or on the surface, so as to deposit or chemically modify a substance on the surface. For example, altering the potential of an electrode may generate an acid which removes an acid labile protecting group from a substance on the surface.

The method described in this specification thus provides a convenient alternative to existing methods for modifying surfaces in local areas. It uses the chemical reactions which occur at the surface of an electrode immersed in a solution of electrolyte. Substances which come into contact with the anode or cathode may be modified by electrochemical reactions. These reactions have been studied over many decades and are now well understood. In the most direct application to patterning a surface the electrode would be placed in direct contact with the surface to be modified and current applied; molecules in the surface which contact the electrode would be subject to electrochemical reaction. Alternatively, the radicals and ions generated in the immediate vicinity of an electrode, either those generated by primary electrolysis, or secondary products generated by interaction of the primary products with the solvent or solutes, may react with an adjacent surface. The location, size and shape of the area that is modified on the surface are determined by the dimensions and position of the electrodes. By contrast with existing methods which use electrochemical processes for electrodeposition or etching, it should be noted that the present method does not require that the surface to be modified forms one of the electrodes, so that the method can be applied to non-conducting materials.

Advantages of the Invention

Electrochemical patterning has a range of applications and potential for automation which give it advantages over many existing methods. The most commonly used method for making small devices is photolithography. In this method, the surface is first coated with a light-sensitive resist, exposed through a mask and the pattern is revealed by etching away the exposed or the unexposed resist and, subsequently, a surface layer. A separate mask must be made for each pattern. There are problems in controlling the etching reaction and in registering masks between each step. Electrolytic patterning can be carried out using a permanent array of independently switched electrodes. An unlimited range of patterns can be created from a dense array of point electrodes, and as will be shown, many complex patterns can be made from a simple array of linear electrodes. Methods for the fabrication of such arrays and circuitry to control the switching are already available. Different shapes can be produced from the same array at different stages in the fabrication by simply switching a different pattern of electrodes without the need to move the array, eliminating the problem of registration. Different effects can be achieved by altering the composition of the electrolyte, the potential applied to the electrodes, and the duration of the electrolytic pulse, giving the method a versatility not found in alternatives. It would also allow for reproducible production of many identical components from the same tool.

Processes for making small devices must be able to render fine detail. The electrolytic method has high resolution and definition; diffusion of the electrode products is limited by barriers created by the electric field, so that the action of the agents is confined to the region of the surface which is directly opposite the electrode which generates them. The resolution is limited by the size of the electrodes. Current technology could make individual electrodes of sub-micron size, arranged in arrays with electrodes at spacings of a few microns.

The range of reagents that can be produced electrochemically includes radicals, radical ions, acids and bases of any strength. Thus a wide range of chemical modifications can be envisaged; for example oxidations and reductions, acid and base catalysed reactions, polymer formation, chemical etching etc. The method may therefore open up possibilities which are difficult or impossible using existing technology. In particular it may be useful for the fabrication of devices carrying arrays of complex chemical substances made by stepwise synthesis, for example chemical sensors; and for the fabrication of hybrid devices, for example, solid state devices which combine on a single surface, sensor molecules and circuitry to measure interactions between sensors and ligands. The fine regulation that can be applied to the electrolytic current provides a degree of control over reactions which is difficult to achieve using conventional reagents and will be an aid to complex fabrication.

As compared with alternatives, the method is simple and versatile, and lends itself readily to automation.

More Detailed Consideration of Some Features of the Method

1. Controlling the Extent of Reaction

The amount of a reagent that is generated at the surface to be modified can be controlled in several different ways. In the examples described below it was regulated by altering the voltage applied to the electrodes. The concentration of protons generated at the anode depended on the anode current; the extent of reaction depended on this concentration and the time for which the ions were kept in contact with the surface. An alternative is to apply voltage to the electrodes until the component ions of the electrolyte have completely separated; in this case, the concentration of reagent generated at the electrode depends on the initial concentration of ions and the total amount of reagent per unit area depends on the depth of liquid between the electrode and the surface to be modified. The extent of reaction on the surface can be limited by the concentration and thickness of the film of electrolyte.

The most powerful way of regulating the extent of reaction exploits the circuitry which is a necessary component of the system. The electrolytic process and the changes to the reactive surface modify the electrical properties of the system. These changes can be monitored and the information used to modulate the voltage or to switch off the current at the end point.

2. Confining the Area Affected by Electrical Caging of Ions

If significant time is needed for the reagent to interact with the surface, it is desirable to prevent the reagent from diffusing away. Ions can be held in place by applying a low potential, sufficient to counteract diffusion but not enough to generate significant amounts of new reagent. This principle has been tested by generating acid at anodes using the method described in the second example. The electrode array was placed against a strip of pH indicator paper. Short pulses of high potential produced faint lines of acid response; long periods of low potential produced no acid response; a short pulse of high potential followed by a longer period at low potential produced a strong acid response in a sharp line; a longer pulse of high potential produced a broader band of acid.

3. Controlling Side Reactions

Electrolysis often produces a discharge of gases at the electrodes and clearly the release of bubbles could present problems as they would stir the reagents away from the gap between the electrode and the reaction site. However, in the physical embodiment envisaged the amount of gas is small because the film of electrolyte is only a few micrometers thick. In the experiment described in the second example below, there was no visible formation of bubbles during the short pulses of applied potential or during the period when the ions were caged at low potential. Any gas that did come out of solution must have formed microscopically small bubbles under the conditions used.

Other undesirable side reactions could include the formation of radicals in reactions where acids or bases are called for. These may be removed by including radical scavengers. Any undesirable generation of acid or base, which may occur for example when the desired reagent is an oxidising or reducing agent, can be prevented by choosing an electrolyte which produces weak acid or base, such as those used in pH buffers.

BRIEF DESCRIPTION OF THE DRAWINGS

Reference is directed to the accompanying drawings in which:

FIGS. 2a) and 2b) show an array of electrodes for use in this invention.

FIG. 2c) is an enlargement of the region circled in 2b), showing ions generated at the anodes and cathodes.

FIG. 2d) is a further enlargement showing acid deprotection induced in contact with the anode.

Example applications

Figures 1, 3:
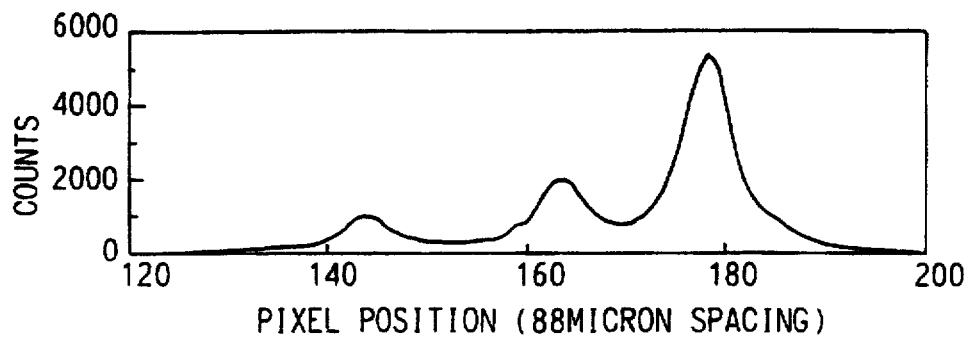
FIG. 1 is a diagram showing a protocol for building an array of all 256 tetranucleotides.
FIG. 3 is a graph of radioactive counts against Pixel position (88 µm spacing).

Novel Devices Carrying Complex Patterns of Chemicals

It is envisaged that electrolytic patterning will find many and diverse applications. As an illustration of the potential in one field, the following section describes a generic set of applications—the fabrication of small devices with many different chemical compounds tethered to the surface. Such devices have potential in chemical and biochemical analyses which measure interactions between specific ligands and test substances. Examples are enzymes with their substrates, antibodies with antigens, drugs with their target receptors, and nucleic acids with oligonucleotides.

For many applications, it is desirable to compare the interactions of large numbers of ligands of related structure, for example peptides or oligonucleotides of different sequence, or drugs with different modifications to a basic structure. Large numbers of analyses are time consuming if carried out one at a time, and moreover, it is difficult to compare reactions done at different times as conditions may vary. These problems are removed if multiple ligands are synthesised on a single surface as they can then be reacted simultaneously with the test substance and analysed together. We have demonstrated the power of this approach by synthesising thousands of oligonucleotides on the surface of a glass plate, hybridising radioactive nucleic acids to them, and analysing the pattern of interactions by autoradiography or phosphorimaging. Such large numbers of analyses, which would take many months of work using conventional methods, can be carried out in a day using a matrix of ligands and parallel processing, and have allowed us to carry out wide ranging analyses of the interactions between oligonucleotides (Maskos and Southern, 1992a and 1992b).

At the present time there is a need for methods of nucleic acid sequence analysis which can be automated so that they can be applied on a large scale (Hunkapiller et al., 1991). Devices carrying complete sets of all sequences oligonucleotides of a given length can be used in sequence analysis. If a nucleic acid molecule is hybridised to such a set, it is possible in principle to determine its sequence, by overlapping those oligonucleotides which give a positive signal. Several authors have considered the theoretical basis of this process (Drmanac and Crkvenjakov, 1987; Bains and Smith, 1988; Lysov et al. 1988; Southern, 1988; (Drmanac et al. 1989; Khrapko et al., 1989; Bains, 1991). The length of sequence that can be analysed by a complete set of oligonucleotides of a given length is approximately the square root of the number of oligonucleotides in the set. Octanucleotides, of which there are 65, 536, may be useful in the range up to 200 bases (Lysov et al., 1988; Khrapko et al., 1989; Pevzner, 1989; Maskos, 1991); and decanucleotides, of which there are more than a million, may analyse up to a kilobase. Despite intensive effort it has proved difficult to fabricate arrays with such large numbers of oligonucleotides.

A method has been developed for synthesising, oligonucleotides in situ using a linker which leaves them covalently attached to the surface of a glass plate and available for hybridisation (Maskos, 1991; Southern and Maskos, 1988), and so the problem to be solved is one of carrying out syntheses in small confined areas. The synthesis of an oligonucleotide is a cyclic process consisting of a coupling step in which a monomer unit for one of the four bases is added to the growing chain. A protecting group is then removed from the 5'-hydroxyl group which becomes available for the addition of the next monomer unit. Different sequences can be made in different regions of a surface by confining the reagent during the coupling step or during deprotection. One approach that has been suggested is to print masks over the surface with patterns specific to each coupling or deprotection step (Southern, 1988). A second starts by making small patches of activated polyacrylamide gel on a glass surface; presynthesised oligonucleotides are attached by applying them to the gel by micromanipulation (Khrapko et al., 1989 and 1991); patches 30×30 μm can be made in this way but it is an extremely slow and difficult process and it is unlikely that large numbers could be made in this way. A third has been to use photolabile protecting groups which are subsequently removed by illuminating the surface through a patterned mask (Fodor et al., 1991) patches ca. 50×50 μm can be treated, but the protecting groups are not very labile and it has not proved possible to make oligonucleotides longer than trimers by this method, though it has been more successful in making oligopeptides. The largest arrays that have been made comprise 4096 oligonucleotides on a surface 200×200 mm (Maskos, 1991). These were made using templates clamped against the surface to form channels through which reagents were passed to irrigate the surface in lines 3 mm wide. Arrays representing all sequences can be built by this procedure using a protocol which applies nucleotide precursors to the surface of the plate in rows and columns; the logic of the procedure is similar to the familiar way of writing the triplet code in which all 64 triplets can be represented just once in 16 rows and four columns. A protocol that could be used to build an array of all 256 tetranucleotides is shown in FIG. 1. This process can be continued to any chosen depth, to produce a two dimensional array of all oligonucleotides of any length in which each oligonucleotide sequence occurs only once. If all four bases are used, $4^s$ oligonucleotides of length s are synthesised in s steps, applying the nucleotide precursors in $\sqrt{4^s/2}$ rows and columns. Other shapes than stripes can be used to make complete sets of oligomers. The same effect could be achieved by nesting quadrants inside squares that decreased in area fourfold at each step.

Referring to FIG. 1, the sequences of four bases in each of the 256 boxes represent a complete set of tetranucleotides. These can be made by applying the base specific precursors in rows and columns. To make this set by the irrigation method, the four bases are first applied in narrow channels in the order A,C,G,T,A,C . . . as indicated. After deprotection of the 5'-hydroxyl by treating the whole plate with acid, the channels are turned through 90° and the precursors applied in the same order. The process is continued in the third and fourth cycles but now the width of the channels is increased to embrace four of the narrower channels.

The protocol can be adapted for electrolytic processing. The device would comprise a set of 16 Pt strips, each switchable between an anode or a cathode. The array would be placed against the derivatised plate and anode current applied to the 'A' channels. This would deprotect the linker in the 1st, 5th, 9th and 13th columns. The electrolyte would be replaced by the precursor for A. After coupling, electrolyte would be introduced and lines 2, 6, 10 and 14 switched to anodes, followed by coupling with C. These would be followed by similar steps for coupling G and T to their columns. A second cycle with the electrodes turned through 90° would produce an array comprising 16 copies of all 16 dinucleotides. The third and fourth bases would be added by a similar process in which A was coupled in the first four columns and rows, C in the second group of four, and so on, to produce an array of all 256 tetranucleotides. Larger sets of longer oligonucleotides can be produced by expanding the groups of lines by a factor of four at each cycle.

A device carrying all octanucleotides made by the existing irrigation procedure would be an unwieldy 750×750 mm. Electrolytic deprotection can produce much smaller cells, as illustrated by the following experiment.

EXAMPLE 1

A standard glass microscope slide was derivatised with an aliphatic linker bearing a primary hydroxyl group at the end of a 20 atom aliphatic chain. A 5'-dimethoxytritylthymidine-H-phosphonate was attached to this hydroxyl by a standard synthetic step (Froehler et al., 1986), over the whole surface of the slide. The slide was immersed in a solution of triethylammonium sulphate in acetonitrile (1% v/v sulphuric acid, 3% v/v triethylamine). A "V" section platinum anode was placed across the slide with the sharp edge resting against the derivatised surface. The cathode was a platinum wire held 10 mm above the anode and parallel to it. Voltage varying from 0.15 to 5 V/mm was applied in pulses between the electrodes for periods varying from 1 to 60 seconds. After each pulse the electrodes were moved along the slide to a new location. Removal of the dimethyoxytrityl groups by the acid generated at the anode exposed 5'hydroxyls on the thymidines which were reacted with $(1-^{14}C)$ acetic anhydride. The slide was exposed to a PhosphorImager screen. The scan showed fine lines of radioactivity running across the slide where the anode had made contact. The intensity of the lines increased with applied voltage, reaching a maximum at 4 V/mm for 1 sec. The peak intensity corresponded to that measured on a control slide which had been treated with dichloroacetic acid under standard conditions for removing the dimethoxytrityl group. The width of the stripes was less than 0.5 mm.

In addition to achieving the desired result of narrow stripes, this example illustrates one advantage of the fine control that electrochemical generation of reagents makes possible, which in this case could lead to much faster reaction cycles. Acid deprotection of dimethoxytrityl groups takes 100 seconds using conventional chemistry; the reaction is carried out slowly because of the difficulty of timing the necessary change of solutions accurately. By contrast, it is easy to apply precisely regulated current in very short pulses and the corresponding electrolytic deprotection was complete in one second.

To make a complete array of oligonucleotides of every possible sequence using the simple protocol described in the caption to FIG. 1, it would be an advantage to be able to have an array of linear electrodes permanently in place; the order of coupling different bases would be determined by switching the appropriate line in sequence.

The following example demonstrates such a device and illustrates some of its important features.

EXAMPLE 2

The surface of a glass microscope slide was derivatised with an aliphatic chain bearing a primary and secondary hydroxyl group (Southern and Maskos, 1988). These groups were reacted with (1-$^{14}$C) acetic anhydride to form acetate esters. An electrode array comprising four parallel platinum strips (0.25 mm wide at 1 mm centres, embedded in epoxy resin and machined to a flat surface) was placed across the slide, with the two surfaces in contact. A small volume of triethylammonium sulphate in acetonitrile (1% v/v sulphuric acid, 3% v/v triethylamine) was run between the array and the slide so that the solution formed a film 5–10 µm in thickness. Electrodes 1, 2 and 4 of the array were connected to a DC supply as cathodes and number 3 was connected as an anode. Pulses of 5 and 10 V/mm were applied between the electrodes for periods varying from 1 to 10 seconds. After each pulse, the electrodes were moved along the slide to a new location. Removal of the (1-$^{14}$C) acetate groups by the acid generated at the anode was seen by exposing the slide to a PhosphorImager screen. The scan showed fine lines clear of radioactivity running across the slide where the anode had made contact. The width of the lines at half height was ca. 200 µm. Some apparent broadening of the band is caused by the detection system; the PhosphorImager screen has a grain size of 100 µm. Short pulses at low voltages gave a lower extent of deprotection than longer pulses at higher voltage. The acetate was completely removed by a pulse of 10 V/mm for 5–10 sec.

Taken together, the two examples illustrate the versatility of the method: dimethoxytrityl groups are highly sensitive to acid whereas acetate esters are only moderately labile. Optimum conditions for removing these groups, using the same electrolyte, were achieved by varying the current intensity and the time of the electrolytic pulse. This shows how different regions of a surface can be modified in a different way simply by applying different potentials to the relevant electrodes, and how sequential steps in layering a surface, or in a complex synthesis, can be carried out without repositioning the array.

Similar procedures can be used to make oligomers other than oligonucleotides, for example oligopeptides or oligosaccharides; the standard synthetic chemistry for synthesising oligopeptides, which uses acid labile protecting groups is appropriate for this method. The principles are not confined to making oligomers of similar subunits, but could be applied to any chemical synthesis, and also to the modification of materials.

The second example illustrates the high resolution and definition which results from the barriers to diffusion created by the electric field. The sulphate ions which accumulate close to the anode are held away from the flanking cathodes by charge repulsion. The action of the acid generated by the sulphate ions is confined to the region of the slide which is directly opposite the anode.

The advantages of the electrolytic procedure over the alternatives of photodeprotection, masked coupling and micromanipulation are readily apparent.

EXAMPLE 3

The fabrication of a 16 element microelectrode array has been achieved and this prototype has been used to demonstrate the viability of electrochemical patterning using electrodes ≈250 µm wide. In the second stage of development this design has been reduced in size and the number of microelectrodes increased to 256. This new array is currently in production and tests to evaluate its performance will commence in the near future.

Method

The primary requirements of the "first generation" microelectrode array are firstly, that it contains a minimum of 256 individual electrodes, each 50–100 µm wide and ≈50 mm in length and secondly that the array is uniformly flat and resistant to both mechanical wear and chemical attack. Two different approaches to fabrication have been investigated: in one the pattern is created by metallic deposition through a mask; in the other the pattern is cut out by detailed mechanical abrasion following a uniform metallic deposition.

i) Masking

Four different arrays each comprised of 16 microelectrodes were designed, drawn and etched into copper. The major problems with the fabrication of microelectrode arrays is that of "fan out", the electrical connection of many closely localised electrodes to an external device, but due to the small number of electrodes in these initial designs it was possible to incorporate a suitable "fan" arrangement on the mask so that the final array would be compatible with a standard circuit board connector. These masks have been successfully used to produce 16 element arrays with 200 µm electrode widths.

ii) Mechanical cutting

This is a simple but effective method of isolating electrodes by using a narrow blade diamond saw to cut shallow groves in a substrate coated with a thin metallic film. Electrode widths of ≈250 µm and separation of ≈250 µm have been routinely produced by this method. The problem of "fan out" however cannot be overcome during definition of the electrode pattern. This problem has been solved by connecting each electrode in turn to a printed circuit board with 50 µm gold wire using an impact bonder and embedding the fragile connections in epoxy resin. Manufacture of even smaller arrays by this method is presently underway using specialised diamond saws capable of defining 50 µm wide grooves.

Both these approaches are capable of producing microelectrode arrays suitable for initial testing. Further reduction in size will rule out mechanical cutting though we favour this as a method of fabrication because it is quick and inexpensive. Furthermore, the shallow channels cut between the electrodes using this method may provide a convenient irrigation system for the electrolyte and other reagents used in the production of the chemical sensors.

Materials

The main materials problem was that of securely bonding an inert metal to an unreactive insulating substrate. This problem has been overcome by depositing ≈1 µm of platinum by electron-beam evaporation onto polished alumina (99.99% Bioceramic grade) followed by an anneal at 1100° C. for 4 hours. At elevated temperatures the platinum diffuses down the grain boundaries of the alumina to form a very adherent coating which has proved to be resistant to both mechanical wear and chemical attack.

Tests of the Electrode Array

The electrode array was first tested using a pH indicator system and shown to produce sharp lines of acid opposite electrodes connected as anodes, and then used in the following experiment. A 5'-O-trityl thymidine-3'-phosphate residue was coupled through the phosphate to a microscope slide which was then clamped against the Pt coated side of the electrode array. Electrolyte (0.01% $H_2SO_4$, 0.03% $Et_3N$ in acetonitrile) was introduced between the slide and the array. 3 V DC was applied for 20, 40 and 80 sec. between single electrodes connected as anodes and the rest of the array which were connected as cathodes. The current, which was initially 30 μA, fell rapidly to 12 μA after about 2 sec. and then decreased slowly.

Hydroxyl groups exposed by acid hydrolysis of the trityl groups were detected by transferring $^{32}$p from y-$^{32}$P-ATP to the hydroxyl groups catalysed by polynucleotide kinase. The isotope was detected in a Molecular Dynamics Phosphor Imager. The image shows clear lines where acid generated at the anode had deprotected the hydroxyl groups. The intensity increased with pulse time and at 80 sec. reached a level equivalent to that produced by standard deprotection in 3% TCA, which is known to be more than 99% complete.

As shown in FIG. 2a), an array of electrodes is based on a block 10 of alumina, the upper surface of which carries a deposited layer 12 of platinum. Grooves 14 have been cut through this top coating into the alumina block, resulting in an array of parallel electrodes 16. The width of each electrode, and of each groove is approximately 250 μm. For the experiment of Example 3, a microscope slide 18 was used, the lower surface of which carried a uniform coating of 5'-O-trityl-thymidine-3'-phosphate residues coupled through the phosphate to the slide.

In FIG. 2b), the slide has been clamped against the platinum coated side of the electrode array.

FIG. 2c) shows the effect of connecting up alternate electrodes 16 as anode and cathode respectively. Et$_3$N$^+$ ions are generated at the cathodes 16a in the electrolyte 20. H$^+$ and SO$_4^-$ ions are generated at the anode 16b in the electrolyte 20. As shown in FIG. 2d), these H$^+$ ions cause deprotection of the thymidine-3'-phosphate residues adjacent the anode.

FIG. 3 is a profile of the radioactive counts generated along three lines of deprotection, in the experiment of Example 3. The peak on the left was deprotected for 20 sec. and the other two for 40 and 80 sec. respectively. Detection of the $^{32}$P by phosphor imaging degrades the image by shine from the radioisotope, accounting for much of the spread of the lines from the expected width of about 250 μm.

References

1. Bains, W. (1991). Hybridisation methods for DNA sequencing. Genomics 11: 294–301.

2. Bains, W., and Smith, G. C. (1988). A novel method for nucleic acid sequence determination. J. theor. Biol. 135: 303–307.

3. Drmanac, R., and Crkvenjakov, R. (1987). Yugoslav Patent Application 570.

4. Drmanac, R., Labat, I., Brukner, I., and Crkvenjakov, R. (1989). Sequencing of megabase plus DNA by hybridisation: Theory of method. Genomics 4: 114–128.

5. Fodor, S. P. A., Read, J. L., Pirrung, M. C., Stryer, L., Lu, A. T., and Solas, D. (1991). Light-directed, spatially addressable parallel chemical synthesis. Science 251: 767–773.

6. Froehler, B. C., Ng, P. G., and Matteucci, M. D. (1986). Synthesis of DNA via deoxynucleoside H-phosphonate intermediates. Nucleic Acids Res. 14: 5399–5407.

7. Hunkapiller, T., Kaiser, R. J., Koop, B. F. and Hood, L. (1991). Large-scale and automated DNA sequence determination. Science 254: 59–67.

8. Khrapko, K. R., Lysov, Yu. P., Khorlyn, A. A., Shick, V. V., Florentiev, V. L., and Mirzabekov. (1989). An oligonucleotide hybridisation approach to DNA sequencing. FEBS Lett. 256: 118–122.

9. Khrapko, K. R., Lysov, Yu. P., Khortin, A. A., Ivanov, I. B., Yershov, G. M., Vasilenko, S. K. Florentiev, V. L. and Mirzabekov, A. D. (1991). A method for DNA sequencing by hybridisation with oligonucleotide matrix. DNA Sequence 1: 375–388.

10. Lysov, Yu. P., Florentiev, V. L., Korlyn, A. A., Khraphko, K. R., Shick, V. V. and Mirzabekow, A. D. (1988). Dokl. Akad. Nauk SSSR 303: 1511–1511.

11. Maskos, U. (1991). A novel method of nucleic acid sequence analysis. D. Phil. thesis, Oxford University.

12. Maskos, U. and Southern, E. M. (1992a). Oligonucleotide hybridisations on glass supports: a novel linker for oligonucleotide synthesis and hybridisation properties of oligonucleotides synthesised in situ. Nucleic Acids REs. 20: in the press.

13. Maskos, U. and Southern, E. M. (1992b). Parallel analysis of oligodeoxyribonucleotide (oligonucleotide) interactions. I. Analysis of factors influencing oligonucleotide duplex formation. Nucleic Acids Res. 20: in the press.

14. Pevzner, P. A. (1989). I-tuple DNA sequencing: Computer analysis. J. Biomolecular Structure and Dynamics 7: 63–73.

15. Southern, E. M. (1988). Analysing Polynucleotide Sequences. International Patent Application PCT/GB89/00460.

16. Southern, E. M. and Maskos, U. (1988). Support-Bound Oligonucleotides. International Patent Application PCT/GB 89/01114.

I claim:

1. A method of treating a region of a surface, which method comprises providing an electrolyte overlying the surface, and an array of electrodes adjacent the surface and in contact with the electrolyte, and altering the potential of one or more of the electrodes of the array so as to deposit or chemically modify a substance on the surface at the regions adjacent those electrodes, wherein one or more of the electrodes of the array are used as counter-electrodes, and the surface to be modified does not form either an electrode or a counter-electrode.

2. The method as claimed in claim 1 wherein, for the purpose of performing several electrochemical treatments in sequence, the electrodes of the array are connected up so that each treatment is performed by altering the potential of a chosen set of one or more of the electrodes of the array.

3. The method as claimed in claim 2, wherein the or each treatment is performed in the course of a stepwise chemical synthesis of an oligomer.

4. The method as claimed in claim 3, wherein the or each treatment is performed by connecting at least one electrode of the array as anode at a potential to remove an acid labile protecting group from a substance on the surface.

5. The method as claimed in claim 1, wherein the surface is electrically insulating.

6. A method of synthesizing a set of oligomers on a surface, by the steps of:
   a) providing a surface carrying a protecting group, an electrolyte overlying the surface and one or more electrodes adjacent regions of the surface and in contact with the electrolyte,
   b) altering the potential of one or more electrodes to remove the protecting group at one or more chosen regions of the surface,
   c) depositing a protected monomer at those regions of the surface from which protecting group has been removed,
   d) and repeating steps b) and c), while varying the region chosen in step b), so as to synthesize a set of oligomers on the surface.

7. The method as claimed in claim 6, wherein the oligomers are oligonucleotides.

8. The method as claimed in claim 6, wherein there is provided in a) an array of electrodes adjacent the surface and in contact with the electrolyte, and the potential of one or more of the electrodes of the array is altered in b).

9. The method as claimed in claim 8, where one or more of the electrodes of the array are used as counter-electrodes.

10. A device comprising an array of electrodes in a form of a block of insulating material having a first surface provided with electrodes spaced apart in an array; electrical conducting means for altering the potential of each said electrode; a body having a second surface to be electrochemically modified, which second surface is electrically insulating; and means for holding the said block of insulating material in spaced relationship with the said body, with the first surface overlying the second surface so as to define therebetween a region for containing electrolyte.

11. The device as claimed in claim 10, wherein the block of insulating material is of an oxide ceramic and the electrodes are of a noble metal.

12. The device as claimed in claim 10, wherein the electrodes are in the form of parallel lines.

13. The device as claimed in claim 12, wherein the parallel lines are spaced apart by no more than 0.5 mm.

* * * * *